(12) United States Patent
Vitullo et al.

(10) Patent No.: US 9,987,449 B2
(45) Date of Patent: Jun. 5, 2018

(54) SUCTION CATHETER DEVICE AND METHOD

(71) Applicant: TELEFLEX MEDICAL INCORPORATED, Research Triangle Park, NC (US)

(72) Inventors: Jeffrey Vitullo, Pottstown, PA (US); Greg Etter, Douglassville, PA (US); Matthew Moore, Ephrata, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 190 days.

(21) Appl. No.: 14/155,002

(22) Filed: Jan. 14, 2014

(65) Prior Publication Data

US 2014/0200554 A1    Jul. 17, 2014

Related U.S. Application Data

(60) Provisional application No. 61/752,126, filed on Jan. 14, 2013.

(51) Int. Cl.
*A61M 16/04* (2006.01)
*A61M 25/00* (2006.01)
*A61B 90/70* (2016.01)

(52) U.S. Cl.
CPC ........ *A61M 16/0463* (2013.01); *A61M 25/00* (2013.01); *A61B 2090/701* (2016.02);
(Continued)

(58) Field of Classification Search
CPC ....... A61B 19/34; A61B 1/267; A61B 1/2676; A61M 16/04; A61M 2209/10;
(Continued)

(56) References Cited

U.S. PATENT DOCUMENTS 3,502,069 A * 3/1970 Silverman .................... 600/587
3,671,979 A * 6/1972 Moulopoulos ............... 623/2.11
(Continued)

FOREIGN PATENT DOCUMENTS

NO    2012/131626 A2    10/2012
NO    2013/030821 A1    3/2013
(Continued)

*Primary Examiner* — Scott Medway
(74) *Attorney, Agent, or Firm* — Baker & Hostetler LLP

(57) ABSTRACT

A device and method for removing material from inside a tube is provided, comprising a catheter having a tubular body and defining an inner lumen, the distal end portion of the tubular body defining a distal opening and apertures on a sidewall. An expandable member is attached to the distal end portion of the catheter tubular body distal to the one or more apertures. The expandable member is capable of having a first unexpanded condition such that the distal opening is open to allow fluid communication with the inner lumen of the catheter through said distal opening, and a second expanded condition such that the distal opening is occluded to prevent fluid communication with the inner lumen of the catheter through said distal opening, the second expanded condition of the expandable member having a maximum transverse diameter larger than a diameter of the tubular body proximal to the expandable member.

8 Claims, 5 Drawing Sheets

(52) U.S. Cl.
CPC .... *A61B 2217/005* (2013.01); *A61M 16/0479* (2014.02); *A61M 2025/0019* (2013.01)

(58) Field of Classification Search
CPC .............. A61M 16/00; A61M 16/0402; A61M 16/0427; A61M 25/0119; A61M 1/0023; A61M 25/0069; A61M 25/007; A61M 25/0071; A61M 25/0075; A61M 29/02; A61M 27/00
See application file for complete search history.

(56) References Cited

U.S. PATENT DOCUMENTS

| | | | | |
|---|---|---|---|---|
| 4,240,433 | A * | 12/1980 | Bordow | 604/540 |
| 4,324,262 | A * | 4/1982 | Hall | 600/569 |
| 4,469,100 | A * | 9/1984 | Hardwick | 606/127 |
| 4,555,242 | A * | 11/1985 | Saudagar | A61F 5/445 604/103.08 |
| 4,606,347 | A * | 8/1986 | Fogarty et al. | 606/194 |
| 4,762,125 | A * | 8/1988 | Leiman et al. | 128/207.15 |
| 4,886,496 | A * | 12/1989 | Conoscenti et al. | 604/103.11 |
| 4,946,440 | A * | 8/1990 | Hall | 604/164.09 |
| 4,961,738 | A * | 10/1990 | Mackin | 606/15 |
| 5,188,618 | A * | 2/1993 | Thomas | 604/267 |
| 5,337,730 | A * | 8/1994 | Maguire | 600/157 |
| 5,360,403 | A * | 11/1994 | Mische | 604/101.02 |
| 5,364,345 | A * | 11/1994 | Lowery et al. | 604/500 |
| 5,545,179 | A * | 8/1996 | Williamson, IV | 606/213 |
| 5,634,937 | A * | 6/1997 | Mollenauer | A61B 17/00234 604/115 |
| 5,709,691 | A * | 1/1998 | Morejon | 606/106 |
| 5,743,258 | A * | 4/1998 | Sato et al. | 128/207.15 |
| 6,270,489 | B1 * | 8/2001 | Wise et al. | 604/508 |
| 7,179,272 | B2 * | 2/2007 | Kieturakis | A61B 17/00234 600/207 |
| 7,789,893 | B2 * | 9/2010 | Drasler et al. | 606/213 |
| 7,819,890 | B2 * | 10/2010 | Russo et al. | 606/200 |
| 7,854,728 | B2 * | 12/2010 | Boyle, Jr. | 604/267 |
| 8,999,074 | B2 * | 4/2015 | Zachar et al. | 134/166 C |
| 9,095,286 | B2 * | 8/2015 | Vazales et al. | |
| 2005/0172971 | A1 * | 8/2005 | Kolobow et al. | 128/207.14 |
| 2007/0021651 | A1 * | 1/2007 | Gobel | A61F 2/0013 600/31 |
| 2008/0066746 | A1 * | 3/2008 | Nelson et al. | 128/200.26 |
| 2008/0167606 | A1 * | 7/2008 | Dann et al. | 604/95.04 |
| 2010/0199448 | A1 * | 8/2010 | Vazales et al. | 15/104.05 |
| 2013/0046332 | A1 * | 2/2013 | Jones et al. | 606/200 |
| 2014/0142496 | A1 | 5/2014 | Lachar et al. | |
| 2014/0246015 | A1 | 9/2014 | Einav et al. | |
| 2015/0133864 | A1 | 5/2015 | Lachar et al. | |
| 2016/0121066 | A1 | 5/2016 | Lachar et al. | |
| 2016/0193439 | A1 | 7/2016 | Lachar et al. | |
| 2017/0106160 | A1 | 4/2017 | Lachar et al. | |
| 2017/0189589 | A1 | 7/2017 | Lachar et al. | |
| 2017/0326317 | A1 | 11/2017 | Lachar | |

FOREIGN PATENT DOCUMENTS

| | | |
|---|---|---|
| NO | 2017/118970 A1 | 7/2017 |
| NO | 2017/199248 A1 | 11/2017 |
| WO | WO 2012131626 A2 * | 10/2012 |

* cited by examiner

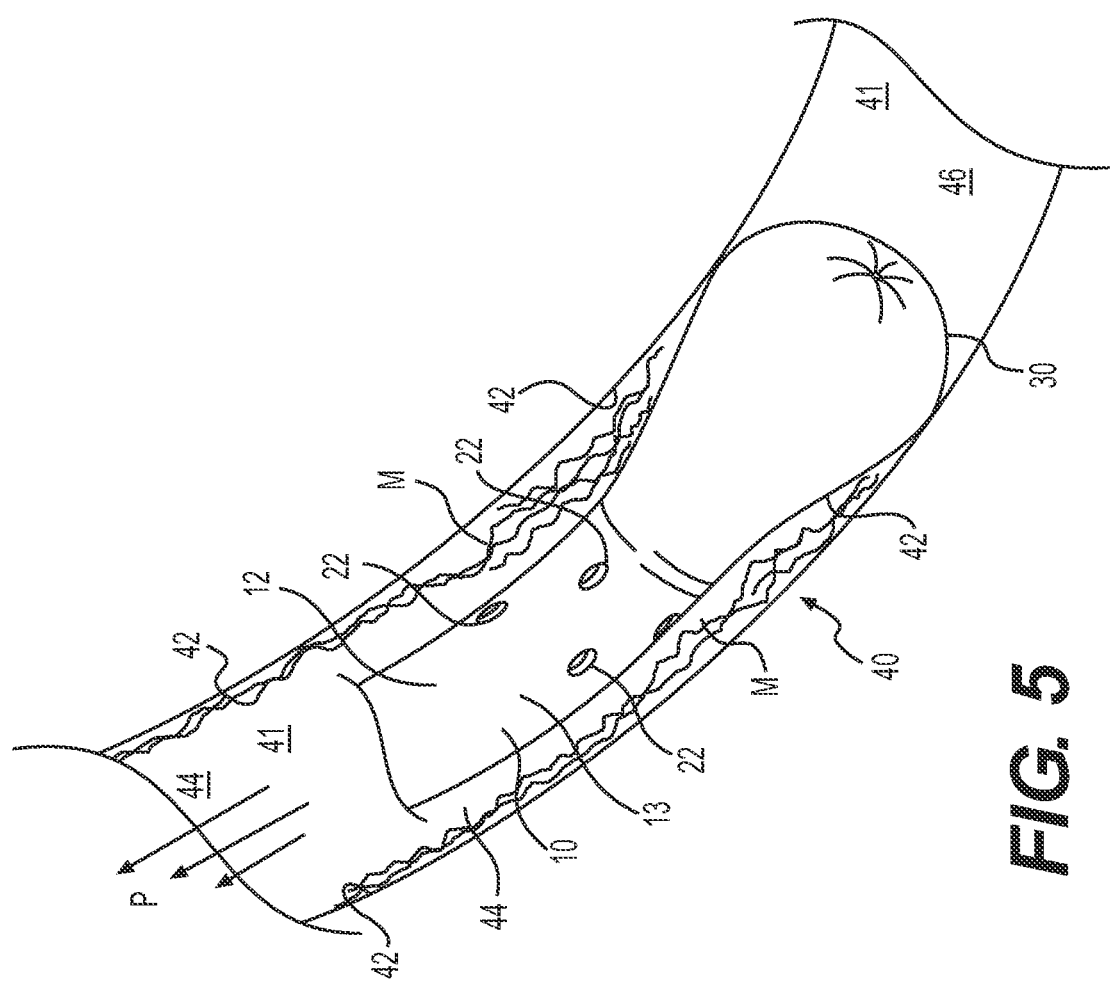

SUCTION CATHETER DEVICE AND METHOD

CROSS-REFERENCE TO RELATED APPLICATION

This application claims priority to U.S. provisional patent application No. 61/752,126, filed on Jan. 14, 2013, the disclosure of which is incorporated by reference in its entirety.

FIELD OF THE INVENTION

The present invention relates to medical devices and in particular a device and methods for use with endotracheal or tracheostomy tubes or laryngeal mask airways, and similar respiratory devices.

BACKGROUND

Endotracheal (ET) tubes, or laryngeal mask airways, or the like, are commonly used for airway management, mechanical ventilation, and as a drug delivery device when intravenous delivery cannot be established. An endotracheal tube is inserted through a process called intubation. During intubation, the endotracheal tube is inserted into the trachea through the patient's opening, either directly through the mouth and throat, or via an incision such as a tracheostomy, in order to keep the airway open and to allow air to reach the lungs. Endotracheal tubes often include a cuff to prevent air leaks during mechanical ventilation. This cuff is most commonly positioned at the distal end of the tube and can be inflatable.

Unfortunately, it is possible for undesirable subglottic secretions to collect around the top of the endotracheal tube's cuff. In order to prevent ventilator-associated pneumonia (VAP), it can be beneficial to remove these secretions by some means. One way to remove these secretions is to remove the endotracheal tube and then re-intubate the patient. However, continued re-intubation can be traumatic to the patient's trachea and is therefore not preferable. Alternatively, suction can be applied to remove these secretions through an additional lumen in the ET tube post intubation. This suction can be applied to remove the accumulated secretions around the outside of the ET tube. However, additional accumulated secretions can collect inside the main lumen of the ET tube itself, which may also need to be removed.

It is therefore desirable to provide a device and method for suctioning these secretions from the inside of the tube without having to remove the endotracheal tube.

An example of a known device for removing material from the lumen of a tube is disclosed in U.S. Pat. No. 4,762,125. This device actually closely resembles an ET tube itself, having a catheter body with an inflatable balloon and apertures proximal thereto for suctioning the material after the balloon is inflated. A problem with this device is that it is not possible to adequately suction the region inside the tube distal to the device or without inflating the balloon.

SUMMARY OF THE INVENTION

As a first embodiment of the present invention, the aforementioned problem is solved in at least a first aspect by a device for removing material from inside a lumen of a tube, comprising a catheter having a tubular body and defining an inner lumen and having a proximal end portion and a distal end portion, the distal end portion of the tubular body defining a distal opening, the proximal end portion of the catheter being configured to couple the inner lumen to a source of suction. The tubular body further defines one or more apertures on a sidewall of the tubular body, the apertures allowing fluid communication with the inner lumen of the catheter from outside the catheter. An expandable member is attached to the distal end portion of the catheter tubular body distal to the one or more apertures. The expandable member is capable of having a first unexpanded condition such that the distal opening is open to allow fluid communication with the inner lumen of the catheter through said distal opening, and a second expanded condition such that the distal opening is occluded to prevent fluid communication with the inner lumen of the catheter through said distal opening, the second expanded condition of the expandable member having a maximum transverse diameter larger than a diameter of the catheter tubular body proximal to the expandable member.

In another aspect of the present invention, the expandable member includes an inflatable member. The inflatable member in an inflated condition is configured to contact and seal against an annular surface of an inner wall of the lumen of the tube into which the device can be inserted, to prevent fluid communication between (i) a proximal region of the lumen proximal to the inflatable member, and (ii) a distal region of the lumen distal to the inflatable member. The inflatable member in an deflated condition does not occlude the distal opening of the catheter tubular body, such that the inner lumen of the catheter is in fluid communication with the distal region of the lumen of the tube; and the inflatable member in the inflated condition occludes the distal opening of the catheter tubular body, such that the inner lumen of the catheter is not in fluid communication with the distal region of the lumen of the tube.

In another aspect of the present invention, the inflatable member defines a sealed expandable inner volume, the inner volume being inflatable by an inflation lumen defined by the device communicating with said inner volume.

In another aspect of the present invention, the inflatable member is circumferentially attached to the tubular body around an annular region of the sidewall on the distal end portion of tubular body, wherein a perimeter of the distal opening of the tubular body is disposed inside the sealed expandable inner volume, the inflatable member being attached to the tubular body proximal to said perimeter.

In one or more other embodiments of the present invention, a method of removing material from inside a lumen of a tube comprises providing a device as recited in one or more aspects of the invention recited above, inserting the catheter into the lumen of the tube, expanding or inflating the expandable member to contact and seal against an annular surface of the inner wall of the lumen of the tube, and to occlude the distal opening of the tubular body, and suctioning through the inner lumen and the one or more apertures to remove material from a region of the lumen of the tube between the catheter and the tube proximal to the expandable member.

In yet another embodiment of the present invention, said method further comprises suctioning through the distal opening of the tubular body into the inner lumen before expanding or inflating the expandable member or after contracting or deflating the expandable member, to remove material from a region of the lumen of the tube distal to the expandable member.

In yet another embodiment of the present invention, said method further comprises pulling the catheter in a proximal direction to move the expandable member in the second expanded condition proximally and in contact along the inner wall of the lumen of the tube to wipe off and/or remove material accumulated on said inner wall.

In yet another embodiment of the present invention, said method further comprises injecting saline into the catheter to exit through the apertures to provide lubrication to the region of the lumen of the tube between the catheter and the tube proximal to the expandable member.

In one or more aspects of the invention, the aforementioned device and methods may be applied to an endotracheal tube, a tracheostomy tube, or a laryngeal mask airway tube.

In one or more aspects of the invention, the aforementioned device and methods may be applied to any tubular body for which it is desirable to remove material accumulated on the inside surface of said body.

There has thus been outlined, rather broadly, certain embodiments of the invention in order that the detailed description thereof herein may be better understood, and in order that the present contribution to the art may be better appreciated. There are additional embodiments and features of the invention that will be described below.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

BRIEF DESCRIPTION OF THE DRAWINGS

FIG. 5 shows the embodiment as shown in FIG. 3 inserted into a tube in the process of removing material inside the lumen of the tube.

DETAILED DESCRIPTION

Figure 1:
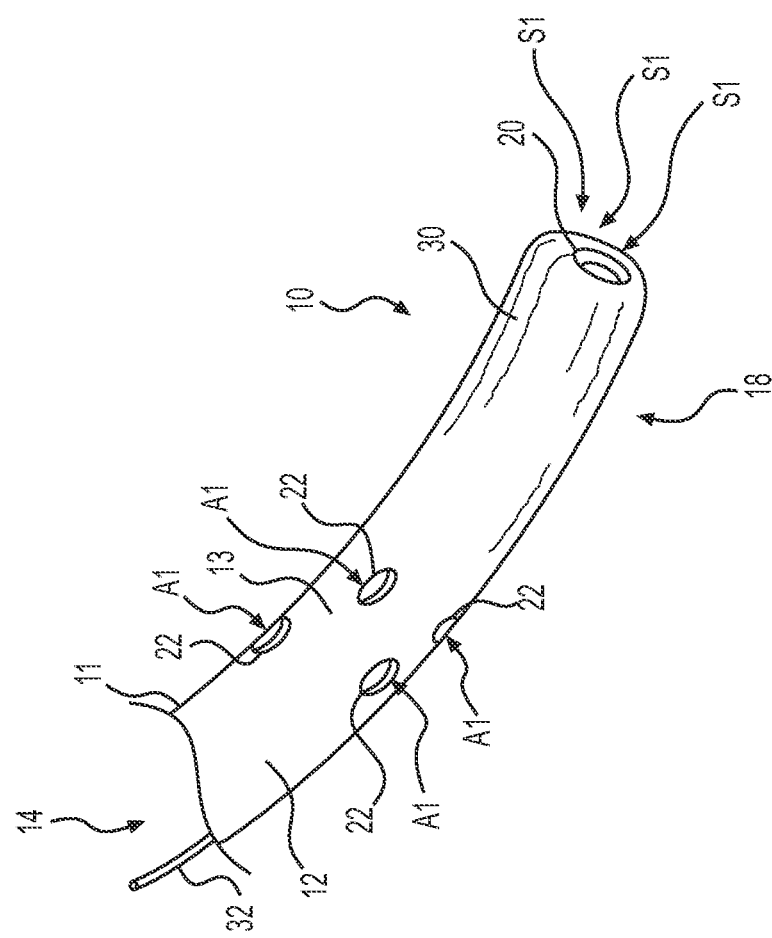
FIG. 1 shows a schematic view of a distal end portion of a suction catheter device in accordance with an embodiment of the present invention, in a first un-expanded, or deflated, condition.

The invention will now be described with reference to the drawing figures, in which like parts are referred to with like reference numerals throughout. In accordance with conventional practice, as used herein, the term "proximal" or "proximal end" shall refer to the specified end of a device or its component which is generally closer to the medical personnel handling or manipulating the device as it is intended to be used, and the term "distal" or "distal end" shall refer to the specified end of a device or its component which is opposite the proximal end. As used herein, the term "longitudinal" shall mean a direction along or spanning the longest dimension of an object, while "transverse" shall mean a direction perpendicular to longitudinal.

Figure 2:
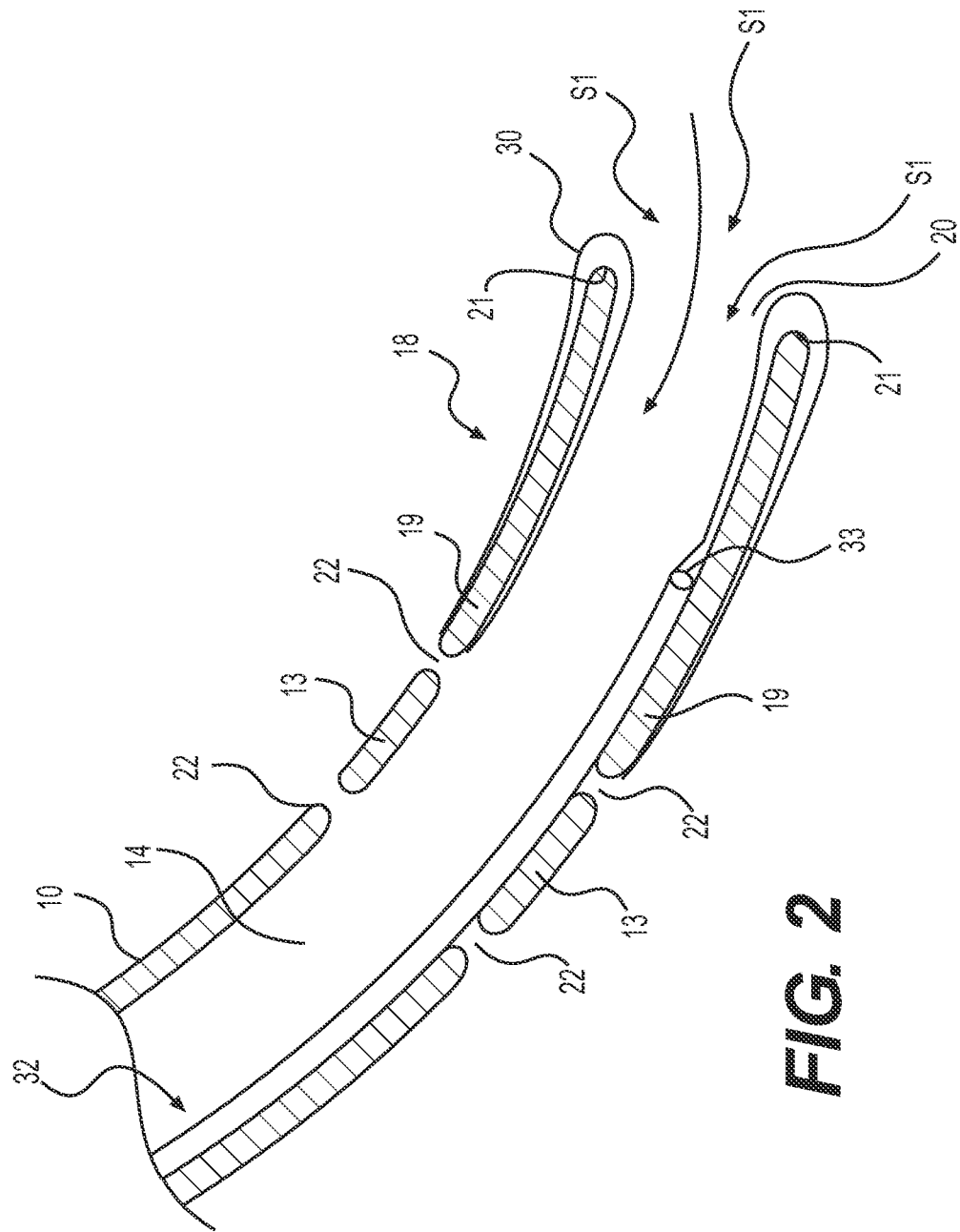
FIG. 2 shows a longitudinal cross-section of the embodiment as shown in FIG. 1.

FIG. 1 shows a schematic view of a distal end portion of a suction catheter device in accordance with an embodiment of the present invention, in a first un-expanded, or deflated, condition. FIG. 2 shows a longitudinal cross-section of the portion of the embodiment as shown in FIG. 1. The device 10 includes a catheter 11 having a tubular body 12 and defining an inner lumen 14 and having a proximal end portion (not shown) and a distal end portion 18. The catheter 11 may be any structure which is flexible enough to be inserted in a device such as an ET tube, and the inner lumen 14 may be any channel, duct, or conduit defined by the device 10 which allows for suctioning or flow of fluid or material within. The proximal end portion may be any suitable configuration having inlet ports or connectors as is well known to one of ordinary skill in the art. The distal end portion 18 of the tubular body 12 defines at least one distal opening 20. In the embodiment shown in FIGS. 1 and 2, preferably one opening 20 is used. The proximal end portion of the catheter 11 is configured to couple the inner lumen 14 to a source of suction, as is well known in the art. The tubular body 12 further defines one or more apertures 22 on a sidewall 13 of the tubular body 12, which are located towards or on the distal end portion 18 of the device 10. Preferably, a plurality of apertures 22 are used, positioned on multiple circumferential positions on the sidewall 13 of the catheter body 12. The apertures 22 allow fluid communication with the inner lumen 14 of the catheter 11 from outside the catheter 11, and thereby enable suction pressure applied to the inner lumen 14 to remove material from outside the catheter 11 through said apertures 22 into said inner lumen 14, as indicated by arrows A1 in FIGS. 1 and 2.

Figure 3:
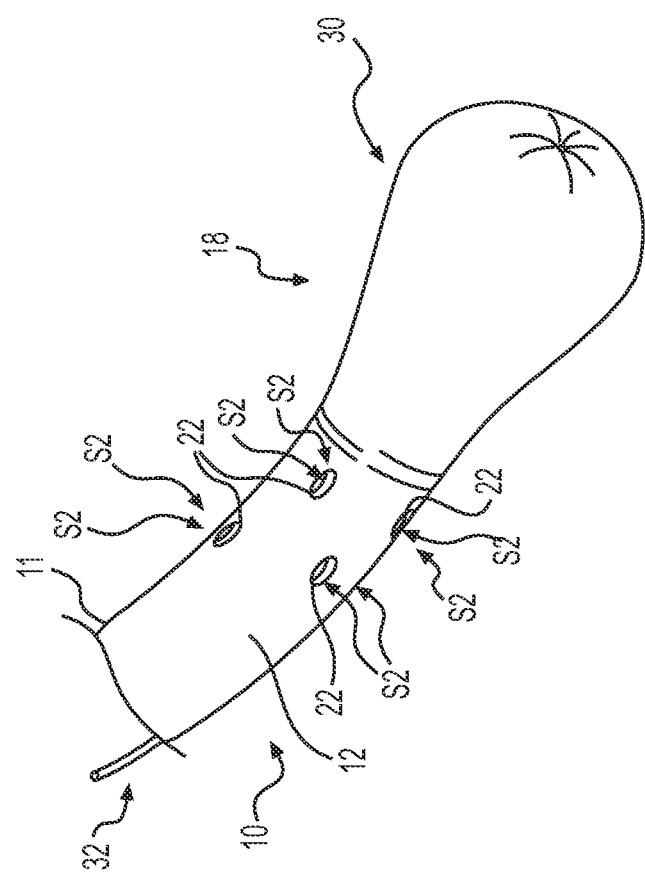
FIG. 3 shows the embodiment shown in FIG. 1, in a second expanded, or inflated, condition.
Figure 4:
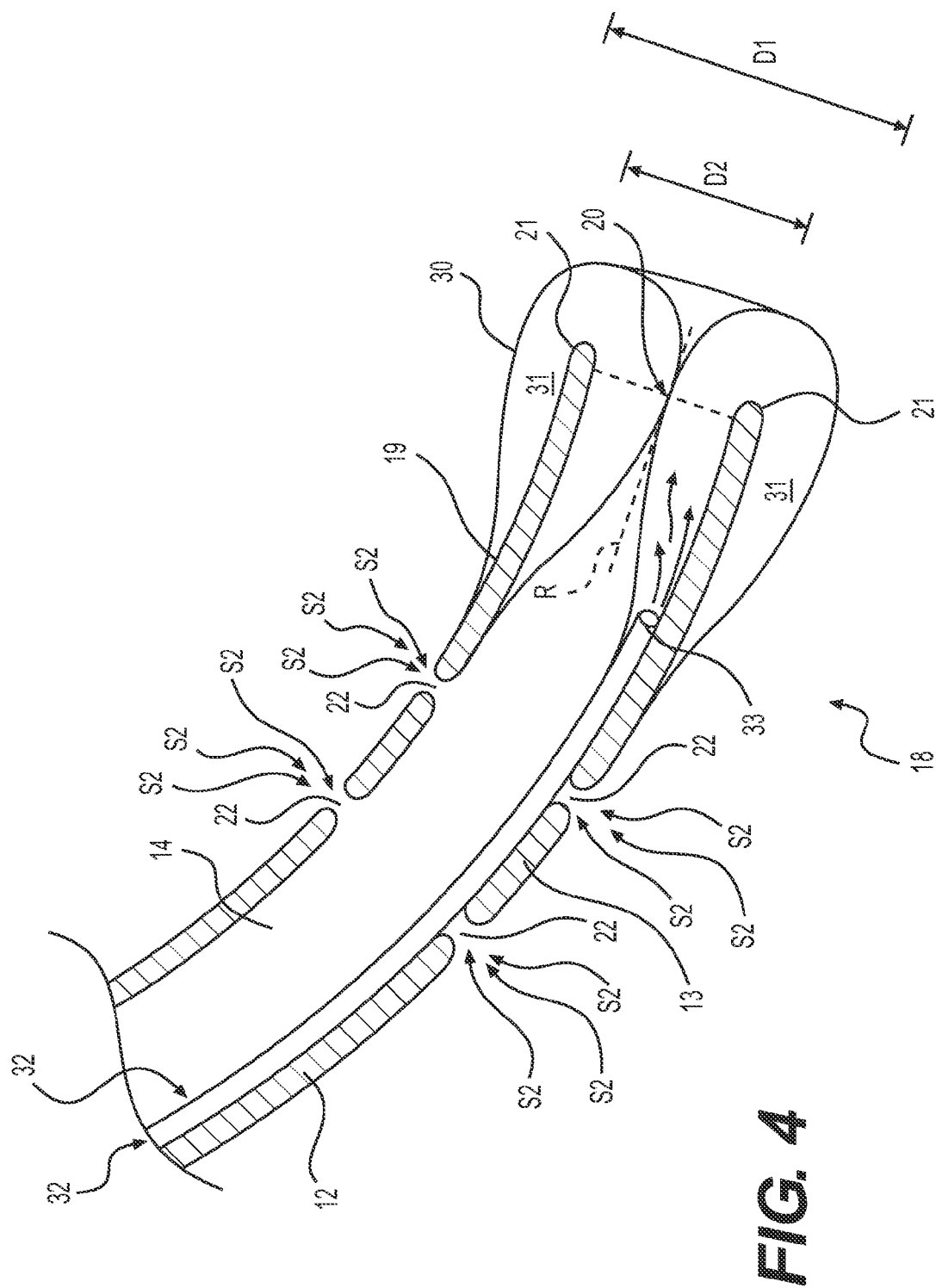
FIG. 4 shows a longitudinal cross-section of the embodiment as shown in FIG. 3.

In the embodiment shown in FIGS. 1-5, an expandable member 30 is attached to the distal end portion 18 of the catheter tubular body 12 distal to the one or more apertures 22. The expandable member 30 is capable of having (i) a first unexpanded condition, as shown in FIGS. 1 and 2, such that the distal opening 20 is open to allow fluid communication with the inner lumen 14 of the catheter 11 through said distal opening 20, and (ii) a second expanded condition, as shown in FIGS. 3 and 4, such that the distal opening 20 is occluded to prevent fluid communication with the inner lumen 14 of the catheter through said distal opening 20. In the first unexpanded condition, suction pressure applied through the inner lumen 14 enables material located distal to the device 10 to be removed through the distal opening 20 as indicated by arrows S1 as shown FIGS. 1 and 2. As shown in FIG. 4, the second expanded condition of the expandable member 30 has a maximum transverse diameter D1 larger than a diameter D2 of the catheter tubular body 12 proximate to the expandable member 30. This enables the device to be applied to contact the inner surface of a tube into which it has been inserted and wipe off or remove material accumulated on said inner surface, as explained further below.

The expandable member can be any structure or a series of structures (such as a plurality of expandable members) which can be changed in form or shape so as to open or occlude one or more openings disposed on the distal end of catheter tube 12, and further expand to a diameter larger than said tube to mate with the inner diameter or surface of a larger tube into which the device 10 is at least partially inserted. In a preferred embodiment of the invention, the expandable member 30 is an inflatable member, although other structures may be used, such as an expandable scaffold or mesh.

When an inflatable expandable member 30 is in an inflated condition, as shown in FIGS. 3-5, it is configured to contact and seal against an annular surface of an inner wall 42 of the lumen 41 of a tube 40 into which the device 10 can be inserted, to prevent fluid communication between (i) a proximal region 44 of the lumen 41 proximal to the inflatable expandable member 30, and (ii) a distal region 46 of the lumen 41 distal to the inflatable member 30, as best shown in FIG. 5. When the inflatable expandable member 30 is in the deflated condition as shown in FIGS. 1 and 2, it does not occlude the distal opening 20 of the catheter tubular body 12, such that the inner lumen 14 of the catheter 11 is in fluid communication with the distal region of the lumen of the tube 46. When the inflatable expandable member is in the inflated condition as shown in FIGS. 3-5, it occludes the distal opening 20 of the catheter tubular body 12, such that the inner lumen 14 of the catheter 11 is not in fluid communication with the distal region 46 of the lumen of the tube, and only suction can be applied to the proximal region 44 through the one or more apertures 22, but not the distal region 46. However the present invention provides the critical advantage that suction can also be applied before the expandable member 30 is expanded or inflated while the catheter 11 is first inserted in the tube 40 from which it is to remove material (or after use in the expanded or inflated state), thereby enhancing its ability to remove material, not simply through its sidewall apertures 22, but also through the distal opening 20. The present invention also efficient in that the expandable member 30 itself is used to both (i) open or close the distal opening 20, and (ii) position the expandable member 30 in an expanded or inflated state against the inner walls 42 of the tube 40 into which the device 10 can be inserted so as to enable the wiping off of material accumulated thereon, while simultaneously isolating suction to the sidewall apertures 22 proximal to the expandable member 30.

In the embodiment shown in FIGS. 1-4, the inflatable expandable member 30 defines a sealed expandable inner volume 31, the inner volume being inflatable by an inflation lumen 32, such as a micro-bore tube, defined by or within the device 10 communicating with said inner volume 31 through an inflation outlet 33 as shown in FIGS. 2 and 4. In one embodiment, the inflation lumen 32 could be formed inside the wall of the catheter tubular body 12.

The present invention as shown in the embodiment in FIGS. 1-5 has a unique and novel configuration wherein the inflatable expandable member 30 is circumferentially attached to the tubular body 12 around an annular region 19 of the sidewall 13 on the distal end portion of tubular body, wherein a perimeter 21 of the distal opening 20 of the tubular body 12 is disposed inside the sealed expandable inner volume 31. The inflatable expandable member 30 is thus attached to the tubular body 12 proximal to said perimeter 21. In one aspect of the present invention, the inflatable expandable member 30 thus defines a substantially toroid shape when expanded or inflated, with the added feature that the upper transverse portion of the toroid is broken in a circumference about the radial axis of the toroid, such as axis R shown in FIG. 4, and implanted onto a mouth or opening of a tube end, such as tubular body 12. In another aspect of the present invention, the inflatable expandable member 30 may define a planar longitudinal cross-section which is dual tear-drop shaped, as best shown in FIG. 4, the inner sealed volume 31 of the member 30 thus being defined as a volume of revolution of said tear-drop shape. Other cross-sectional shapes are possible, provided the expandable member 30 is attached to the distal end of tube 12 so as to open and occlude the distal opening 20 of said tube.

The present invention also provides a method of removing material from inside a lumen of a tube. The method provides a device 10 as described in the embodiments herein, which is inserted into the lumen of a tube 40. Next the expandable member 30 is expanded or inflated to contact and/or seal against an annular surface of the inner wall 42 of the lumen 41 of the tube, and to occlude the distal opening 20 of the tubular body 12. Suction is applied through the inner lumen 14 and the one or more apertures 22 to remove material from the region 44 of the lumen of the tube between the catheter 11 and the tube 40 proximal to the expandable member 30. The method may further include suctioning through the distal opening 20 of the tubular body 12 into the inner lumen 14 before expanding or inflating the expandable member 30 or after contracting or deflating the expandable member 30, to remove material from the region 46 of the lumen 41 of the tube 40 distal to the expandable member 30, as indicated by arrows S1 in FIGS. 1 and 2. The method may further comprise pulling the catheter 11 in a proximal direction P to move the expandable member 30 in the second expanded condition proximally and in contact along the inner wall 42 of the lumen 41 of the tube 40 to scrape or wipe off and/or remove material M accumulated or adhered on said inner wall 42, and subsequently through the apertures 22, as indicated by arrows S2 in FIGS. 3 and 4. The method may also include a step of injecting a fluid, such as saline, into the catheter to exit through the apertures 22 so as to create lubrication assist in removal of material from inside of the tube. In one embodiment the method may include injecting a bolus of saline into the catheter in its inflated position whereby saline departs through the apertures 22 to create lubrication prior to starting suction and pulling back the catheter. The fluid such as saline may be included in another lumen or tube provided in or adjacent the catheter body 12.

The method of the present invention may be applied to an endotracheal tube, a tracheostomy tube, or a laryngeal mask airway tube. Alternatively, the method could be applied to any tube having an inner lumen.

The device 10 can be made from materials including medical grade plastics such as polyvinyl chloride, latex or polyurethane or other suitable materials for the device and methods disclosed herein.

The dimensions of the device can vary. As a non-limiting example, the diameter of a tube for adults would typically be 12, 14 or 16 Fr, pediatrics/neonatals would be 5 Fr. The diameter of inflatable member would be compliant and fit to the inner diameter of the target ET Tube.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention. All ranges cited herein specifically incorporate all values and sub-ranges within the cited range.

The invention claimed is:

1. A device for removing material from inside a lumen of a tube, comprising:
   a catheter having a tubular body and defining an inner lumen and having a proximal end portion and a distal end portion defining a distal end of the tubular body, the distal end of the tubular body having a perimeter which defines a distal opening of the inner lumen, the proximal end portion of the catheter being configured to couple the inner lumen to a source of suction;

the tubular body further defining one or more apertures on a sidewall of the tubular body, the apertures allowing fluid communication with the inner lumen of the catheter from outside the catheter, the apertures being disposed on the tubular body proximal to the distal opening of the inner lumen;

an expandable member attached to the distal end portion of the catheter tubular body distal to the one or more apertures, the expandable member being capable of having a first unexpanded condition such that the distal opening is open to allow fluid communication with the inner lumen of the catheter through said distal opening, and a second expanded condition such that the distal opening is occluded to prevent fluid communication with the inner lumen of the catheter through said distal opening, the second expanded condition of the expandable member having a maximum transverse diameter larger than a diameter of the catheter tubular body proximal to the expandable member;

wherein the expandable member is an inflatable member; and wherein the inflatable member in an inflated condition is configured to contact and seal against an annular surface of an inner wall of the lumen of the tube into which the device can be inserted, to prevent fluid communication between (i) a proximal region of the lumen proximal to the inflatable member, and (ii) a distal region of the lumen distal to the inflatable member; and wherein the inflatable member in a deflated condition does not occlude the distal opening of the catheter tubular body, such that the inner lumen of the catheter is in fluid communication with the distal region of the lumen of the tube; and wherein the inflatable member in the inflated condition occludes the distal opening of the catheter tubular body, such that the inner lumen of the catheter is not in fluid communication with the distal region of the lumen of the tube, wherein the inflatable member defines a sealed expandable inner volume, the inner volume being inflatable by an inflation lumen defined by the device communicating with said inner volume, wherein the inflatable member is circumferentially attached to the tubular body around an annular region of the sidewall on the distal end portion of tubular body, wherein the perimeter defining the distal opening of the distal end of the tubular body is disposed inside the sealed expandable inner volume, the inflatable member being attached to the tubular body only proximal to said perimeter defining said distal opening, and wherein the inflatable member is at least partially expanded within the inner lumen of the tubular body in the inflated condition.

2. A method of removing material from inside a lumen of a tube, comprising:

providing a device for removing material from inside a lumen of a tube, the device comprising a catheter having a tubular body and defining an inner lumen and having a proximal end portion and a distal end portion defining a distal end of the tubular body, the distal end of the tubular body having a perimeter which defines a distal opening of the inner lumen, the proximal end portion of the catheter being configured to couple the inner lumen to a source of suction;

the tubular body further defining one or more apertures on a sidewall of the tubular body, the apertures allowing fluid communication with the inner lumen of the catheter from outside the catheter, the apertures being disposed on the tubular body proximal to the distal opening of the inner lumen;

an expandable member attached to the distal end portion of the catheter tubular body distal to the one or more apertures, the expandable member being capable of having a first unexpanded condition such that the distal opening is open to allow fluid communication with the inner lumen of the catheter through said distal opening, and a second expanded condition such that the distal opening is occluded to prevent fluid communication with the inner lumen of the catheter through said distal opening, the second expanded condition of the expandable member having a maximum transverse diameter larger than a diameter of the catheter tubular body proximal to the expandable member;

inserting the catheter into the lumen of the tube, expanding or inflating the expandable member to contact and seal against an annular surface of the inner wall of the lumen of the tube, and to occlude the distal opening of the tubular body; and suctioning through the inner lumen and the one or more apertures to remove material from a region of the lumen of the tube between the catheter and the tube proximal to the expandable member;

wherein the inflatable member in an inflated condition is configured to contact and seal against an annular surface of an inner wall of the lumen of the tube into which the device can be inserted, to prevent fluid communication between (i) a proximal region of the lumen proximal to the inflatable member, and (ii) a distal region of the lumen distal to the inflatable member; and wherein the inflatable member in a deflated condition does not occlude the distal opening of the catheter tubular body, such that the inner lumen of the catheter is in fluid communication with the distal region of the lumen of the tube; and wherein the inflatable member in the inflated condition occludes the distal opening of the catheter tubular body, such that the inner lumen of the catheter is not in fluid communication with the distal region of the lumen of the tube;

wherein the inflatable member defines a sealed expandable inner volume, the inner volume being inflatable by an inflation lumen defined by the device communicating with said inner volume;

wherein the inflatable member is circumferentially attached to the tubular body around an annular region of the sidewall on the distal end portion of tubular body, wherein the perimeter defining the distal opening of the distal end of the tubular body is disposed inside the sealed expandable inner volume, the inflatable member being attached to the tubular body only proximal to said perimeter defining said distal opening, and wherein the inflatable member is at least partially expanded within the inner lumen of the tubular body in the inflated condition.

3. The method of claim 2, further comprising suctioning through the distal opening of the tubular body into the inner lumen before expanding or inflating the expandable member or after contracting or deflating the expandable member, to remove material from a region of the lumen of the tube distal to the expandable member.

4. The method of claim 2, wherein the tube is an endotracheal tube, a tracheostomy tube, or a laryngeal mask airway tube.

5. The method of claim 2, further comprising pulling the catheter in a proximal direction to move the expandable member in the second expanded condition proximally and in contact along the inner wall of the lumen of the tube to wipe off and/or remove material accumulated on said inner wall.

6. The method of claim 5, further comprising suctioning through the distal opening of the tubular body into the inner lumen before inflating the expandable member or after contracting or deflating the expandable member, to remove material from a region of the lumen of the tube distal to the expandable member.

7. The method of claim 6, wherein the tube is an endotracheal tube, a tracheostomy tube, or a laryngeal mask airway tube.

8. The method of claim 2, further comprising:
    injecting saline into the catheter to exit through the apertures to provide lubrication to the region of the lumen of the tube between the catheter and the tube proximal to the expandable member.

\* \* \* \* \*